US006642425B2

(12) United States Patent
Winder et al.

(10) Patent No.: US 6,642,425 B2
(45) Date of Patent: Nov. 4, 2003

(54) REACTIVE DISTILLATION PROCESS FOR THE ALKYLATION OF AROMATIC HYDROCARBONS

(75) Inventors: J. Barry Winder, Austin, TX (US); Donald L. Wharry, Austin, TX (US); John R. Schell, Austin, TX (US); Mary J. Brown, Cedar Park, TX (US); Joy L. Murray, Austin, TX (US); Richard C. Howe, Round Rock, TX (US); Wayne L. Sorensen, Austin, TX (US); Daniel P. Szura, Georgetown, TX (US)

(73) Assignee: Sasol North America Inc., Houston, TX (US)

( * ) Notice: Subject to any disclaimer, the term of this patent is extended or adjusted under 35 U.S.C. 154(b) by 0 days.

(21) Appl. No.: 10/091,199

(22) Filed: Mar. 5, 2002

(65) Prior Publication Data

US 2003/0171630 A1 Sep. 11, 2003

(51) Int. Cl.⁷ ........................... C07C 15/067; C07C 2/64
(52) U.S. Cl. ........................ 585/323; 585/446; 585/470; 585/449; 585/450
(58) Field of Search ............................... 585/446, 470, 585/449, 450, 323

(56) References Cited

U.S. PATENT DOCUMENTS

| | | | |
|---|---|---|---|
| 5,019,669 A | 5/1991 | Adams et al. | 585/446 |
| 5,082,990 A | 1/1992 | Hsieh et al. | 585/467 |
| 5,113,031 A * | 5/1992 | Sy | 585/467 |
| 5,258,560 A | 11/1993 | Marker | 568/697 |
| 5,362,377 A * | 11/1994 | Marker | 208/133 |
| 5,476,978 A * | 12/1995 | Smith et al. | 585/323 |
| 5,770,782 A | 6/1998 | Knifton et al. | 585/467 |
| 5,866,736 A * | 2/1999 | Chen | 585/323 |
| 6,002,058 A * | 12/1999 | Hearn et al. | 585/448 |
| 6,315,964 B1 | 11/2001 | Knifton et al. | 422/190 |

* cited by examiner

Primary Examiner—Walter D. Griffin
Assistant Examiner—Tam M. Nguyen
(74) Attorney, Agent, or Firm—Browning Bushman P.C.

(57) ABSTRACT

A unified process for reactive distillation under pressure for the alkylation of light aromatic hydrocarbons such as benzene and cumene with straight chain $C_6$–$C_{18}$ olefins using a solid acid alkylation catalyst supported in the reflux zone of the distillation column. The process is continuous, using a reactive distillation configuration such that at least a portion of the olefin is injected below the benzene rectification zone at the top of the column. The aromatic hydrocarbon is injected continuously at a low rate above the rectification zone at the base of the column and above the reboiler. The alkylation reaction takes place primarily in the liquid phase on the solid acid catalyst and is characterized in that the molar ratio of aromatic hydrocarbon to olefin in the liquid phase may be adjusted. The molar ratio is adjustable up to about 100/1, through adjustment of the internal column operating pressure, the benzene reflux rate, the amount of benzene removed from the reflux condenser to storage or from the reboiler with the distillation column operated at or near total aromatic hydrocarbon reflux. The unexpectedly high liquid phase aromatic hydrocarbon to olefin molar ratios achieved in the reactive distillation column increases the selectivity to mono-alkylated aromatics and helps stabilize catalyst lifetime.

18 Claims, 1 Drawing Sheet

REACTIVE DISTILLATION PROCESS FOR THE ALKYLATION OF AROMATIC HYDROCARBONS

FIELD OF THE INVENTION

This invention relates to an alkylation process. More particularly, this invention relates to the alkylation of aromatic hydrocarbons with olefins in a continuous, pressurized, reactive distillation process employing a solid alkylation catalyst system.

BACKGROUND OF THE INVENTION

Linear alkylated aromatic compounds have many uses of significant commercial value. For example, alkylated light aromatic compounds, such as benzene and cumene, have value as gasoline octane enhancers. Aromatic compounds alkylated with long chain (that is, having greater than about 10 carbon atoms) linear olefins are commonly sulfonated to produce surfactants suitable for use in detergent manufacture.

The chemical reactions involving alkylation of aromatics with olefins have been studied for a long time. For example, U.S. Pat. No. 2,860,173 discloses the use of a solid phosphoric acid as a catalyst for the alkylation of benzene with propylene to produce cumene. More recently, the use of Friedel Crafts catalysts, especially aluminum chloride and certain natural zeolites and synthetic commercial sieves, as alkylation catalysts, has been taught.

Commercially, alkylation of aromatics is frequently carried out in reactive distillation processes associated with the reformulation of gasoline. However, there continue to be problems associated with commercial alkylation processes. These include low yields of the desired alkylated products, a tendency to produce poly-substituted aromatics, and catalyst "coking", that is, the building up of carbonaceous deposits and heavy organics on the catalyst surface, with resultant decrease in catalyst effectiveness and a need to shut the process down to regenerate. Most of these problems are directly related to the exothermic nature of the reaction, which has a tendency to be difficult to control. As a result there has appeared to have been a limit to the amount of aromatic hydrocarbon that can be practically introduced into the system, even when co-fed with the olefin introduction. Most commercial alkylation using HF alkylation technology employ an aromatic hydrocarbon to olefin mole ratio in the range of 4/1–8/1. More recently, it has been proposed in fixed bed solid acid alkylation processes to use molar ratios up to 30/1. The ability to adjust this molar ratio over a wider range without increasing the flow of aromatic hydrocarbon into the process can provide significant advantage in enabling the selective production of mono-alkylated product as opposed to the di-alkylated product, which is known to cause more rapid deactivation of solid acid catalysts. Minimizing the amount of poly-alkylated product using much higher molar ratios of aromatic hydrocarbon to olefin in the reaction zone holds the potential of helping improve catalyst effective lifetime.

It is clear that a need exists for a method of alkylation of aromatics with olefins, particularly straight chain olefins, that has high olefin conversion rates, a high selectivity for mono-substituted products and prolonged catalyst effectiveness.

SUMMARY OF THE INVENTION

This invention provides a solution to one or more of the problems described above. More particularly, the invention provides a process and a system useful in the preparation of mono-alkylated aromatic compounds by the solid acid-catalyzed reaction of aromatic hydrocarbons compounds with olefins, particularly low molecular weight, straight chain olefins.

In one aspect, the invention is a system comprising a reactive distillation column including a reactive zone, a first rectification zone at the top of the distillation column and a second rectification zone below said reactive zone and further containing a solid acid alkylation catalyst supported in the reactive zone. Positioned below and in communication with the reactive zone through the second rectification zone is a reboiler and means for withdrawing alkylated aromatic compound from the reboiler. Suitably positioned injectors allow for the controlled introduction of aromatic hydrocarbon and olefin feed streams into the reactive zone such that the reactants flow counter-currently to each other in the liquid phase.

In a second aspect, the invention is a continuous reactive distillation process that comprises introducing into a reactive zone, at a point in the distillation column just above the catalyst zone and below a first rectification zone, at least a portion of the olefin containing feedstock and introducing an amount of aromatic hydrocarbons into the reactive zone, at a point below the catalyst zone but above a second rectification zone where it may be refluxed into the reactive zone such that the aromatic hydrocarbon flows upward and contacts the olefin as the olefin liquid phase descends and flows through the catalyst in the reactive zone, whereby the olefin and aromatic hydrocarbon react, in the liquid phase, to form an alkylated aromatic compound.

DETAILED DESCRIPTION OF PREFERRED EMBODIMENTS

Figure 1:
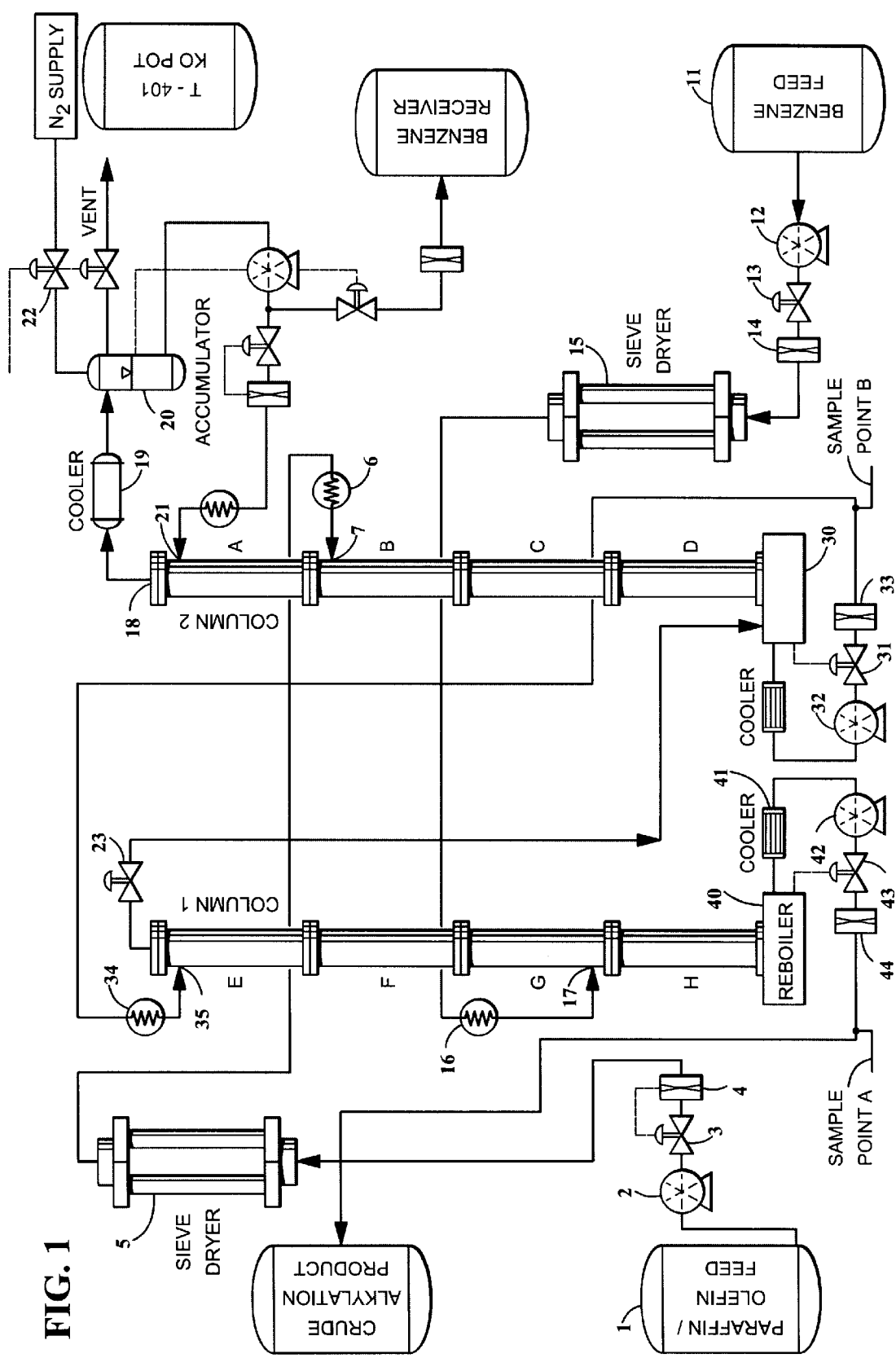
FIG. 1 provides a schematic representation of the continuous reactive distillation system of the invention as two separate and connected columns performing as a single system.

By "light aromatic" or "aromatic", we mean organic aromatic compounds having one or more rings and from 6 to about 30 carbon atoms, preferably 6–20 carbon atoms, that boil at or below about 250° C. under pressure conditions typical in a commercial reactor-type distillation column. The preferred members of this group are benzene, toluene, xylene, styrene, phenol and cumene, with benzene being especially preferred.

The preferred olefins useful in this invention include those straight-chain and/or mono methyl branched, mono-unsaturated olefins having from 6 to about 30 carbon atoms, preferably from about 8 to about 20 carbon atoms and, more preferably, from 10 to 14 carbon atoms. The preferred olefin feed is a $C_6$–$C_{18}$ paraffin, $C_6$–$C_{18}$ olefin, mixture that is derived from a commercial paraffin dehydrogenation process.

The conditions of the subject reactive distillation process require that the internal pressure in the reactive zone be maintained substantially constant and above about 1 atmosphere, preferably between about 20 and about 200 psig. In addition, the combination of aromatic hydrocarbon, unreacted olefin, alkylated aromatics and other by-products, in the reboiler, is maintained at or near total reflux, such that the temperature in the reboiler stays below the thermal degradation temperature of the alkylated product, which is about 265° C., and the molar ratio of the aromatic hydrocarbon to the olefin in the liquid phase is between about 20/1 to about 100/1, preferably between about 30/1 to about 80/1. Under these conditions, the reboiler liquid should preferably be maintained to contain at least 2% by weight aromatic hydrocarbon and the introduction of the aromatic hydrocarbon into the distillation column maintained at a feed rate which is between about 1/6 to about 1/2 the feed rate of the olefin into the distillation column.

The invention involves a continuous process using a reactive distillation configuration such as depicted in FIG. 1. With reference to FIG. 1, the olefin feed is injected below the benzene rectification zone at the top of the distillation column, but above the catalyst zone. In the preferred embodiments illustrated in the examples below, the olefin feed is an olefin/paraffin mixture derived from the dehydrogenation of paraffins. The aromatic hydrocarbon feed is continuously injected at a point below the solid catalyst reactive zone and above the second rectification which keeps the alkylated product from tending to re-enter the reactive zone. The second rectification zone is in communication with and above a reboiler. The second rectification zone ensures that the aromatic hydrocarbon can be separated from the alkylated product, paraffin and unreacted olefin that descends from the reactive zone on its way to the reboiler.

The alkylation reaction takes place primarily in the liquid phase on the solid catalyst in the reactive zone of the distillation column. Non-limiting examples of catalysts that may be employed for this invention include such well known acid zeolitic materials as beta-zeolite, acidic mordenite, acid clays, such as montmorillonite and medium pore zeolites such as ZSM-5, ZSM-12, ZSM-18, ZSM-20, MCM-22, and Beta, L, Y, as well as rare earth exchanged forms or de-aluminated forms of the listed zeolites. Other catalysts that may be employed in the practice of this invention include the fluorided versions of the above-mentioned zeolites and aluminum chloride impregnated on alumina, clays and silica-alumina. The catalyst can be maintained in place by supporting it on structured packing, such as Koch-Glitch KATAMAX brand catalytic structured packing, or alternatively arranged in other ways familiar to those skilled in this art, for example, in a series of beds on perforated trays or in beds positioned in the liquid down corners of a trayed distillation column.

Maintaining the molar ratio of the aromatic hydrocarbon to the olefin in the liquid phase of the reactive zone at significantly higher levels than the stoichiometric amount is an important aspect of the present invention. The molar ratio can be adjusted and maintained, when the system is otherwise operating at steady state at or approaching total reflux, through adjustment of the column internal back pressure, the aromatic hydrocarbon reflux rate, the energy input into the reboiler, the amount of aromatic hydrocarbon separated in the rectifier, the amount of alkylated aromatic hydrocarbon removed, and the input flow of aromatic hydrocarbon.

Coupling the reflux rate of the aromatic hydrocarbon with the relatively low rate of introduction of new aromatic hydrocarbon into the column will tend to increase the composition of aromatic hydrocarbon refluxing into the reactive zone. Together with counter current flow of the liquid. phase olefin, generating and maintaining the higher mole ratios of aromatic hydrocarbon to olefin in the reactive zone has been demonstrated to have several unexpected advantages:

First, the higher aromatic compound to olefin mole ratios tend to allow for a larger reactive zone with more exposed catalyst, which, in turn, tends to stabilize the reaction and make it essentially isothermal in the distillation column. Prior attempts to keep an isothermal process typically involved mixing the aromatic hydrocarbon with the feed of the olefin/paraffin mixture. While this may be done in the system of the present invention, it is less critical.

Second, higher energy input to the reboiler so as to produce the higher reflux rates will be without the risk of exceeding the higher temperatures that can occur in the reboiler, i.e., temperatures exceeding 265° C., at which thermal degradation of the alkylated products begins to take place. High aromatic hydrocarbon reflux rates at constant energy input will tend to decrease the reboiler temperature as they force more aromatic hydrocarbon into the reboiler. Raising the internal pressure within the column can then achieve higher catalyst reaction temperatures, thereby increasing yield, without the risk of exceeding a thermal degradation temperature in the reboiler.

Third, the higher aromatic hydrocarbon to olefin molar ratios, as well as the isothermal nature of the reaction zone, can help increase the usable life of the catalyst. The higher selectivity of the process of this invention for the mono-substituted alkylation, as opposed to poly-alkylation, which is known to poison most solid acid alkylation catalysts, will require less frequent catalyst regeneration.

DESCRIPTION OF APPARATUS, PROCEDURES AND CONDITIONS

In the examples set forth below, the process of this invention was carried out in a continuous reactive distillation column as depicted in FIG. 1. As in the FIG. 1 configuration, for convenience, two separate columns were employed and designed to perform as a single reactive distillation column. Differential pressure control established vapor transport between the lower half (column 1) and the upper half (column 2). Liquid transport between upper segments (column 2) and lower segments (column 1) was handled by a pump and flow control from the base of column 2.

The catalysts employed were a solid acid zeolites, of acidic mordenite and Y. The catalyst is granulated to a 16×40 U.S. mesh size, dried at an appropriate temperature to activate it, and loaded into 54 KATAMAX catalyst packing elements. Each packing element has a 2 inch outside diameter and is 5.5 inches long. The mass of catalyst loaded into the column will depend on its density. However, since the KATAMAX elements all had the same internal catalyst volume (50.8 cc each), the catalyst was equally distributed in the column reactive zone by using 9 KATAMAX elements in each of Sections B, C, D, E, F, and G. The paraffin/olefin feed, as described in Example 1, below, was derived from a paraffin dehydrogenation process. As shown in FIG. 1, that olefin feed is pumped from a storage tank 1 using pump 2. Flow is controlled by control valve 3 and mass flow monitored by a Micro Motion Mass Flow sensor 4.

The paraffin/olefin mixture passes through a 4A molecular sieve bed 5 prior to preheater 6. The olefin injection temperature is adjusted to match the measured reflux temperature inside the column at the point of injection. The point of injection 7 is just above the KATAMAX catalyst elements in Section B, which is just below Section A, the rectification zone that separates and refluxes the aromatic hydrocarbon (which, in each of the examples, is benzene). It will be understood that in addition to injection of olefin feedstock at this point, it can be injected at one or more additional points into the catalyst zone and in any event above the point at which the benzene is injected. This is particularly advantageous when the olefin feedstock is essentially pure olefin.

The aromatic hydrocarbon is pumped from a storage tank 11 using pump 12, with flow controlled by control valve 13 and mass flow monitored using sensor 14. Prior to injection, the aromatic hydrocarbon is also passed through a molecular sieve dryer 15 and is heated at 16 to about 5–10° C. below its boiling point at the internal column pressure. Thus, it is injected as a liquid, but generally will quickly flash due to the heat from the liquid and vapor rising out of the reboiler. As depicted in FIG. 1, the injection point 17 of the aromatic hydrocarbon is at the base of Section G, but above the rectification zone (Section H) which is immediately above the reboiler. This is the primary injection point and sets up the counter-current flow of aromatic hydrocarbon with the olefin descending as a liquid from its injection point (at 7, above the catalyst in Section B).

The aromatic hydrocarbon flows as a vapor through the catalyst in the reactive zone and continues to the top of Section A, where it exits the column at 18. After condensation in Cooler 19, and accumulation in vessel 20, the aromatic hydrocarbon is reinjected at 21, in rectifier Section A. The desired operating pressure is adjusted and maintained using cascade control with nitrogen injection (at control valve 22) in association with the reheating and reinjection of the aromatic hydrocarbon. The aromatic hydrocarbon is maintained in the vapor phase by heating, if necessary, and flow between column 1 to column 2 using a differential pressure, usually no more than about 2 psig, and is controlled by control valve 23.

Paraffin, unreacted olefin, crude alkylated product and equilibrium phase aromatic hydrocarbon are removed after passing through Section D to an accumulator 30. From there, the accumulated liquid is pumped to the top of Section E, 35, where it continues passing through the reactive zone. Care should be taken here to assure that the liquid from Section D is returned to the same reflux temperature at the injection point at the top of Section E. After passing through Sections, F, G, and H, into the reboiler, crude alkylated aromatic product, paraffin, high molecular weight bottoms and unreacted olefin, if present, are removed through the reboiler 40 on level control and pumped to storage through cooler 41, using pump 42, control valve 43 and mass flow sensor 44.

As depicted, there are two sample points for the crude alkylation product. Sample point A is the final product, which has passed through all catalyst sections. Sample point B is an intermediate product, representing approximately 50% of the catalyst residence time. A third sample point, not shown, may be used to check purity of the aromatic hydrocarbon from accumulator 20. Also, in the system used for the examples, the rectification zones above the catalyst in Section B and above the reboiler (Section H) are also packed with KATAMAX packing elements, but containing no catalyst. This was to assure efficient evaporation/condensation in the rectification zones.

The reactive distillation process of the accompanying examples operates using a counter-current flow of benzene injected at the base of the reactive distillation column, a mixture of paraffin and olefin injected above the catalyst zone, variable benzene reflux rates, and variable reboiler energy input. Very high (between about 30 to about 80) benzene/olefin molar ratios in the reactive catalyst zone were achieved by adjusting the reflux rates and the energy input to the reboiler. At the same time, the reboiler temperature remained below that at which product degradation begins to occur.

The higher reflux rates and increased benzene/olefin molar ratios also increased the usable catalyst alkylation temperature range in the reactive zone from 80° C. at atmospheric pressure to 165° C. at 90 psig. The ability to adjust the benzene/olefin molar ratio in the reaction zone imparts a significant and unexpected flexibility to tailor the operating conditions to best suit the solid acid alkylation catalyst being employed.

EXAMPLE 1

This example illustrates process flexibility in terms of the range for the molar ratio between the aromatic hydrocarbon and the olefin that can be achieved in the system of the present invention. A reactive distillation process using the configuration set forth in FIG. 1 was utilized. A counter-current flow of benzene injected at the base of the reactive distillation column, a mixture of paraffin plus olefin injected above the catalyst zone, coupled with variable benzene reflux rates and variable reboiler energy input was employed. The point of paraffin/olefin injection is at the top of section B just above the catalyst zone as depicted in FIG. 1, at 7. Benzene is injected below the catalyst zone (Sections B, C, D, E, F and G). Benzene reflux is also injected at the top of the column in Section A, above the catalyst zone. Energy input into the reboiler is from an electric stab-in heater. Higher kilowatts indicate higher energy required to increase the refluxrate. Reboiler temperature was measured by a stab-in thermocouple positioned in the reboiler liquid. At a 50 psig column pressure and a constant 2.85 kilowatt energy input, the reflux rate is decreased from 196 g/min to 112 g/min. The reboiler temperature rises rapidly and exceeds the 265 degree C. temperature for the onset of thermal degradation. The liquid phase benzene to olefin ratio in the column also decreases as does the benzene content in the reboiler. Reducing the energy input to 2.34 kilowatts reduces the reboiler temperature while maintaining the benzene to olefin molar ratio in the reaction zone of the column at 46/1. A similar trend is observed at 35 psig column pressure where the reboiler energy input needs to be reduced to 1.98 kilowatts while still maintaining a liquid phase benzene/olefin mole ratio of 41/1 in the catalyst zone.

This experiment indicates that the benzene/olefin mole ratio can be adjusted from 27/1 to 76/1 at 50 psig column pressure and a uniform reaction temperature of 142–145 degrees C. and similarly at 35 psig from 26/1 to 77/1 at a uniform reaction temperature of 134 degrees C. As the column pressure is increased to 75 psig, even at total reflux rates of 209 g/min., the reboiler temperature exceeds the thermal degradation temperature of the alkylated product. Energy input needs to be reduced, which begins to limit the liquid phase benzene/olefin mole ratio in the column. At 75 psig, the reboiler temperature can be brought back into an acceptable range when the column benzene/olefin mole ratio is reduced. Increasing the reaction temperature in the catalyst zone above 160 degrees C. will require further increases in column pressure and further reduce the maximum attainable liquid phase benzene/olefin mole ratio. Decreasing the operating pressure will further decrease the catalyst zone temperature, but the full range of liquid phase benzene/olefin mole ratios remains possible since there is no risk of exceeding the thermal degradation temperature. For example, at 25 psig in a relatively high reboiler energy input of 2.34 kilowatts, a benzene/mole ratio of 55/1 was achieved at an acceptable reboiler temperature.

Tables 1 and 2, set forth below, provide the data developed in this example.

TABLE 1

Capillary GC Analysis of Paraffin/Olefin Feed

| | Feed | |
|---|---|---|
| | A Weight % | B Weight % |
| <C10 | 0 | 0 |
| C10 | 1.53 | 1.98 |
| C11 | 3.85 | 3.71 |
| C12 | 3.83 | 3.83 |
| C13 | 2.45 | 2.44 |
| C14 | 0.33 | 0.36 |
| C15 | 0 | 0 |
| Total Olefin | 11.99 | 12.32 |
| Linear Paraffin | | |
| C10 | 0.18 | 0.07 |
| C10 | 14.42 | 19.09 |
| C11 | 31.84 | 29.72 |
| C12 | 26.43 | 24.88 |
| C13 | 14.42 | 13.25 |
| C14 | 0.62 | 0.48 |
| C15 | 0.19 | 0.2 |
| Total Paraffin | 88.1 | 87.69 |
| Avg MW (g/mole) | 163.6 | 162.9 |
| Bromine No. (Cg/g) | 10.8 | 10.4 |

TABLE 2

| Lower Benzene Injection Rate g/min | Paraffin + Olefin Injection Rate g/min | Column Pressure (psig) | Average Catalyst Zone Temp. (C.) | Reboiler Energy Input (KW) | Reboiler Temp (C.) | Reflux Benzene Injection Rate g/min | Liquid Phase Benzene Olefin Mole Ratio | Benzene in Reboiler wt % |
|---|---|---|---|---|---|---|---|---|
| 10 | 50 | 75 | 157 | 2.88 | 306 | 209 | 63 | 3.9 |
| 20 | 50 | 75 | 157 | 2.24 | 262 | 115 | 23 | 19.2 |
| 10 | 50 | 50 | 145 | 2.85 | 253 | 196 | 76 | 17 |
| 10 | 50 | 50 | 145 | 2.85 | 275 | 149 | 58 | 12.3 |
| 10 | 50 | 50 | 145 | 2.85 | 290 | 112 | 42 | 4.7 |
| 10 | 50 | 50 | 145 | 2.34 | 251 | 113 | 46 | 21.4 |
| 10 | 50 | 50 | 143 | 1.98 | 246 | 65 | 27 | 18.2 |
| 10 | 50 | 35 | 134 | 2.88 | 251 | 199 | 77 | 18.7 |
| 10 | 50 | 35 | 134 | 2.34 | 275 | 104 | 32 | 5.9 |
| 10 | 50 | 35 | 134 | 1.98 | 236 | 137 | 41 | 38 |
| 10 | 50 | 35 | 134 | 1.98 | 248 | 51 | 26 | 16.2 |
| 10 | 50 | 25 | 122 | 2.34 | 236 | 167 | 55 | 26 |

EXAMPLE 2

Varying the liquid phase benzene/olefin mole ratio can influence the amount of less desirable bottoms products that will be created for a given solid acid catalyst. These bottoms products can be di-alkylated or poly-alkylated benzene, olefin dimers and polymers as well as di-phenyl alkanes. The amount of bottoms products created is somewhat dependent on the nature of the solid acid catalyst, but can be significantly influenced by the liquid phase benzene/olefin mole ratio in the reactive catalyst zone, as demonstrated in Example 1. The reactive distillation column alkylation system of the present invention can generate a wide range of liquid phase benzene/olefin molar ratios. This can be seen in Table 3, which shows that as the liquid phase benzene/olefin mole ratio is decreased, the amount of bottoms increases. This is shown as the decreasing ratio of alkylated product yield divided by the bottoms yield. This same trend is observed for two different catalysts and at two different reaction temperatures. CBV-20A is a commercial acidic mordenite and TOSOH 330 is an acid Y-zeolite. Both catalysts were chopped and screened to a 16×40 mesh size for loading into the KATAMAX structured catalytic distillation packing elements. The amount of CBV-20A loaded into 54 KATAMAX elements was 1721.26 g. The amount of the TOSOH 330 Y catalyst loaded into an equal number of elements was 1379.27 g. Paraffin/olefin Feed A from Table 1 was used in the investigation of the CBV-20A and paraffin/olefin Feed B was used for the TOSOH Y zeolite.

TABLE 3

| Catalyst | Column Pressure (psig) | Catalyst Reaction Zone Temp (C.) | Paraffin & Olefin Rate (g/min) | Benzene Rate (g/min) | Benzene Reflux Rate (g/min) | Liquid Phase Benzene/ Olefin Mole Ratio | Olefin Conv (%) | 2-Phenyl Alkylate (%) | Linear Alkylate (%) | Product Aklylate/ Bottom Wt. Ratio |
|---|---|---|---|---|---|---|---|---|---|---|
| CBV-20A | 35 | 134 | 49.4 | 14.7 | 146.7 | 56 | 90 | 75.5 | 89.5 | 78.5 |
| CBV-20A | 35 | 136 | 49.1 | 29.8 | 215.3 | 116.5 | 89.1 | 77.5 | 91.4 | 132.4 |
| Tosoh 330-Y | 35 | 135 | 49.8 | 9.9 | 199 | 77.5 | 98 | 21.1 | 91.4 | 83 |
| Tosoh 330-Y | 35 | 135 | 49.9 | 9.8 | 104.5 | 32 | 98.6 | 21.4 | 90.5 | 46.5 |
| Tosoh 330-Y | 50 | 144 | 49.2 | 9.9 | 196 | 76.3 | 98.3 | 21.5 | 91.4 | 66 |

TABLE 3-continued

| Catalyst | Column Pressure (psig) | Catalyst Reaction Zone Temp (C.) | Paraffin & Olefin Rate (g/min) | Benzene Rate (g/min) | Benzene Reflux Rate (g/min) | Liquid Phase Benzene/ Olefin Mole Ratio | Olefin Conv (%) | 2-Phenyl Alkylate (%) | Linear Alkylate (%) | Product Aklylate/ Bottom Wt. Ratio |
|---|---|---|---|---|---|---|---|---|---|---|
| Tosoh 330-Y | 50 | 145 | 50 | 9.9 | 148.9 | 58.3 | 98.5 | 21.7 | 91.0 | 68 |
| Tosoh 330-Y | 50 | 146 | 49.7 | 9.9 | 111.8 | 42 | 98.2 | 22.2 | 88.8 | 45 |
| Tosoh 330-Y | 50 | 150 | 99.7 | 9.8 | 150.8 | 22.9 | 100 | 21.5 | 88.0 | 29.5 |
| Tosoh 330-Y | 35 | 129 | 49.8 | 9.9 | 137.3 | 38.5 | 100 | 20.9 | 89.5 | 33 |

Modifications of the apparatus, procedures and conditions disclosed herein that will still embody the concept of the improvements described should readily suggest themselves to those skilled in the art, and are intended to be encompassed within the spirit of the invention presently disclosed herein as well as the scope of the appended claims.

What is claimed is:

1. A process for the continuous preparation of monoalkylated aromatic compounds in a reactive distillation column including a reactive zone, a first rectification zone at the top of the distillation column and a second rectification zone below said reactive zone and further containing a solid acid alkylation catalyst supported in the reactive zone, said process comprising:
   A. introducing into the distillation column, at a point just above the catalyst zone and below said first rectification zone at least a portion of an olefin feedstock selected from the group consisting of $C_6$–$C_{18}$ olefins and a $C_6$–$C_{18}$ olefins/paraffins mixture;
   B. introducing into the distillation column, at a point below the catalyst zone but above said second rectification zone, an amount of aromatic hydrocarbon having from about 6 to about 30 carbon atoms, such that the aromatic hydrocarbon flows upward and contacts the olefin feedstock in the liquid phase as it descends and flows through the catalyst zone, said second rectification zone including a reboiler;
   C. maintaining an internal pressure in the reactive zone and the combination of olefin feedstock and aromatic hydrocarbon at reflux in said reboiler such that the temperature in the reboiler stays below about 265° C., and wherein the molar ratio of the aromatic hydrocarbon to the olefin in the liquid phase is between about 20/1 to about 100/1.

2. The process of claim 1, wherein the reboiler liquid contains at least 2% by weight aromatic hydrocarbon.

3. The process of claim 1, wherein the pressure in the reactive zone is substantially constant and above about 1 atmosphere.

4. The process of claim 1, wherein the column pressure, as measured below the reactive zone, is between about 20 and about 200 psig.

5. The process of claim 1, wherein the molar ratio of the aromatic hydrocarbon to the olefin in the liquid phase is between about 30/1 to about 80/1.

6. The process of claim 1, wherein introduction of the aromatic hydrocarbon into the distillation column is maintained at a feed rate which is between about 1/6 to about 1/2 the feed rate of the olefin into the distillation column.

7. The process of claim 1, wherein said aromatic hydrocarbon contain from about 6 to 20 carbon atoms.

8. The process of claim 1, wherein a portion of the olefin feedstock is injected into the catalyst zone.

9. A process for the continuous preparation of alkylated aromatic compounds comprising:
   introducing at least a portion of an olefin containing feedstock at a point between an intermediate catalyst zone and an upper rectification zone;
   introducing an aromatic compound having from 6 to 30 carbon atoms at a point between said catalyst zone and a lower rectification zone;
   refluxing said aromatic compound upwardly through said catalyst zone to react, in the liquid phase, with descending olefin feedstock in said catalyst zone to produce alkylated aromatic compounds, the internal pressure in said catalyst zone being above about 1 atmosphere;
   separating said aromatic compound from said olefin feedstock and alkylated aromatic compounds in said lower rectification zone;
   refluxing and separating said aromatic compound in said upper rectification zone; and
   recovering an alkylated aromatic product mixture comprising alkylated aromatic compounds unreacted olefin feedstock and by-product as a bottom stream from said lower rectification zone.

10. The process of claim 9, wherein said olefin-containing feedstock comprises $C_6$–$C_{18}$ olefins.

11. The process of claim 10, wherein said olefin-containing feedstock comprises a $C_6$–$C_{18}$ olefin/paraffin mixture.

12. The process of claim 8, wherein said lower rectification zone includes a reboiler.

13. The process of claim 9, wherein said bottoms stream is recovered from said reboiler.

14. The process of claim 13, wherein the temperature in said reboiler is stabilized below a temperature at which thermal degradation of said alkylated aromatic compounds occurs.

15. The process of claim 9, wherein said catalyst zone contains a supported, solid acid catalyst.

16. The process of claim 9, wherein the pressure, as measured below the catalyst zone is between about 20 and about 200 psig.

17. The process of claim 9, wherein the molar ratio of aromatic compound to olefin in said liquid phase is between about 20/1 to about 100/1.

18. The process of claim 9, wherein the introduction of said aromatic compound is maintained at a feed rate which is between about 1/6 to about 1/2 the feed rate of the olefin present in the olefin feedstock.

* * * * *